United States Patent [19]

Hughes et al.

[11] Patent Number: 5,070,022
[45] Date of Patent: Dec. 3, 1991

[54] ENZYMIC PROCESS FOR PREPARING LEUKOTRIENE ANTAGONISTS

[75] Inventors: David L. Hughes, Old Bridge; Paul J. Reider, Westfield, both of N.J.; Joseph S. Amato, Brooklyn, N.Y.; James J. Bergan, Piscataway; Edward J. J. Grabowski, Westfield, both of N.J.

[73] Assignee: Merck & Co., Inc., Rahway, N.J.

[21] Appl. No.: 288,216

[22] Filed: Dec. 22, 1988

[51] Int. Cl.$^5$ ............................................. C12P 41/00
[52] U.S. Cl. ................................... 435/280; 435/122; 435/130; 435/134; 435/135; 546/174; 546/175
[58] Field of Search ............... 435/122, 130, 134, 135, 435/280; 546/174, 175

[56] References Cited

FOREIGN PATENT DOCUMENTS 233763 8/1987 European Pat. Off. ............ 546/175
271287 6/1988 European Pat. Off. ............ 546/174
63-245694 10/1988 Japan ................................... 435/130

OTHER PUBLICATIONS

Santaniello et al., *J. Org. Chem.*, 53, 1567–1569, (1988).
Whitesides et al., *Angew. Chem. Int. Ed. Engl.*, 24, 617–638, (1985).
Adachi et al., *CHIMA*, 40, No. 9 (Sep.) (1986).
Seebach et al., *CHIMA*, 40, No. 9 (Sep.) (1986).
Guanti et al., *Tetrahedron Letters*, vol. 27, No. 38, 4639–4642, (1986).
Wang et al., *Enzymes in Organic Synthesis, Pitman, London (CIBA Foundation Symposium III)* 128–145, (1985).
Hughes et al., Synthesis of Chiral Dithioacetals: A Chemoenzymic Synthesis of a Novel LTD$_4$ Antagonist, Submitted to the *Journal of Organic Chemistry*.
Levin et al., *Syn. Comm.*, 12, 989–993, (1982).
Saksena et al., *Tetrahedron Letters*, vol. 26, No. 52, 6427–6430, (1985).
Perchonock et al., *J. Med. Chem.*, 28, 1145–1147, (1985).
Perchonock et al., *J. Med. Chem.*, 29, 1442–1452, (1986).
Gleason et al., *J. Med. Chem.*, vol. 30, No. 6, 959–961 (1987).
Jones, *Tetrahedron*, vol. 42, No. 13, 3351–3403, (1986).
Young et al., *Adv. Prostaglandin, Thromboxane, Leukotriene Res.*, 16, 37–45, (1986).

*Primary Examiner*—Carolyn Elmore
*Attorney, Agent, or Firm*—Gabriel Lopez; Joseph F. DiPrima

[57] ABSTRACT

Disclosed is a process for preparing the R and S enantiomers of a compound of the formula:

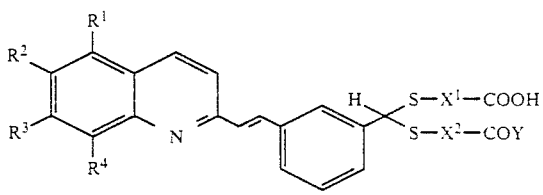

which comprises;
(1) reacting an enzyme with a prochiral diester of the formula

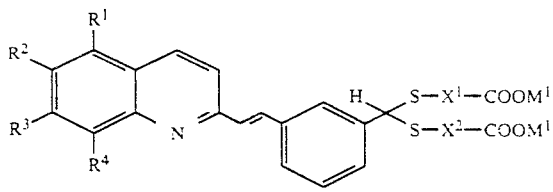

where $M^1$ and $M^2$ are the same, to produce a chiral monoester of the compound of formula II;

(2) treating the chiral monoester product of step (1) with an amine and a trialkyl aluminum compound to produce the R enantiomer of the compound of formula I; or reacting the chiral monoester product of step (1) with an acid activating agent, an amine, and a base to produce the S enantiomer of the compound of formula I.

In the alternative the R enantiomer of the compound of formula I may be synthesized by direct enzymatic hydrolysis of the racemic mixture of a compound having the formula

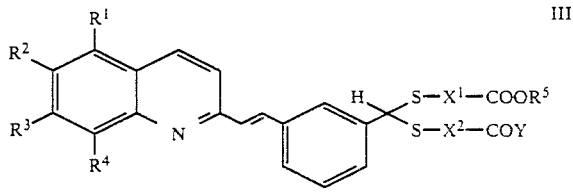

10 Claims, No Drawings

ENZYMIC PROCESS FOR PREPARING LEUKOTRIENE ANTAGONISTS

BACKGROUND OF THE INVENTION

The present invention is concerned with a process for preparing the R and S enantiomers of substituted dithioacetal quinolines via the enzymatic hydrolysis of a substituted dithioacetal quinoline prochiral diester to form the corresponding substituted dithioacetal quinoline chiral monoester from which these R and S enantiomers are formed.

The invention is also concerned with the direct enzymatic hydrolysis of a racemic mixture of a substituted dithioacetal quinoline monoester to yield the R enantiomer of the desired compound.

It has been known in the art to use enzymes to hydrolyze prochiral diesters to form the corresponding chiral monoester. Pig liver esterase has been shown to be an effective enzyme in hydrolyzing meso diesters and diacetates to produce chiral compounds from which the R and S enantiomers of a compound may be formed. Guanti et al., Tet. Lett., 4639–4642, (1986). Santaniello et al., J. Org. Chem. (1988), 53 1567–1569 discusses the enzymatic hydrolysis of prochiral 3-substituted glutarate diesters utilizing pig liver esterase to form the corresponding chiral monoester compounds. Whitsides et. al., Angew. Chem. Int. Ed. Engl. 24 (1985) 617–638 discusses generally the use of enzymes as catalysts in synthetic organic chemistry. The present invention provides a unique way of forming chiral dithioacetal quinoline monoesters by enzymatic hydrolysis of the corresponding prochiral diesters from which the R and S enantiomers of the dithioacetal quinoline monoester may be formed in high yields at low costs. The present invention also provides a process for synthesizing the R enantiomers of a substituted dithioacetal quinoline by a direct enzymatic hydrolysis of a racemic mixture of a substituted dithioacetal quinoline monoester. These are improvements over the prior processes used to produce these compounds.

SUMMARY OF THE INVENTION

The present invention provides a process for producing the R and S enantiomers of a compound of the formula:

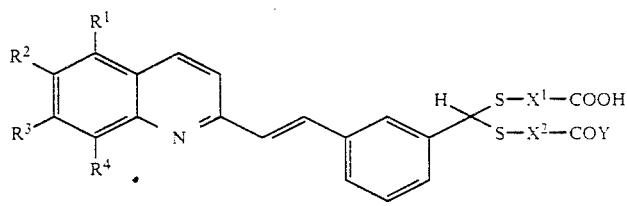

wherein
$R^1$, $R^2$, $R^3$ and $R^4$ are independently selected from the group consisting of hydrogen, chlorine, fluorine or bromine;

$X^1$ and $X^2$ are independently selected from the group consisting of a $C_1$–$C_8$ straight or branch chained alkyl, a $C_2$–$C_8$ straight or branch chained alkenyl, or a $C_2$–$C_8$ straight or branch chained alkynyl, and Y is $NR^6R^7$ where $R^6$ and $R^7$ are independently selected from the group consisting of hydrogen, a $C_1$–$C_8$ straight or branch chained alkyl, a $C_2$–$C_8$ straight or branch chained alkenyl, a $C_2$–$C_8$ straight or branch chain alkynyl;

which process comprises:
(a) reacting an effective amount of an enzyme with a compound of the formula:

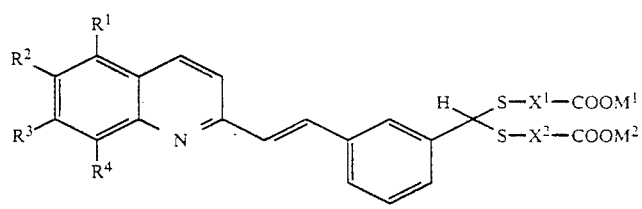

wherein $R^1$, $R^2$, $R^3$, $R^4$, $X^1$ and $X^2$ are as previously defined; and $M^1$ and $M^2$ are the same and are selected from the group consisting of a $C_1$–$C_8$ straight or branch chained alkyl, a $C_2$–$C_8$ straight or branch chained alkenyl, a $C_2$–$C_8$ straight or branch chained alkynyl, $-CH_2COOCH_2CH_3$, $-CH_2CONH_2$, $-CH_2CON(CH_2CH_3)_2$ or $-CH_2CH_2OCH_3$;

to form a compound of the formula;

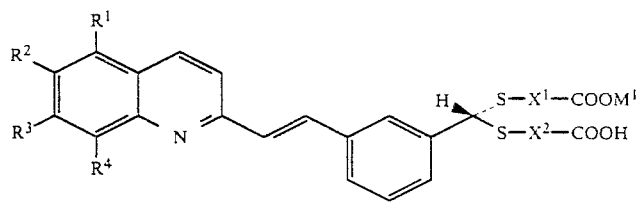

wherein $R^1$, $R^2$, $R^3$, $R^4$, $X^1$, $X^2$ and $M^1$ are as previously defined;

(b) reacting the compound of formula VI with an amine of the formula $HNR^6R^7$ where $R^6$ and $R^7$ are previously defined, and a trialkyl aluminum compound of the formula $AlR^8R^9R^{10}$ where $R^8$, $R^9$ and $R^{10}$ are the same and are a $C_{1-12}$ alkyl group; to form the R enantiomer of a compound of formula IV; or reacting the compound of formula VI with an acid activating agent, an amine of the formula $HNR^6R^7$ where $R^6$ and $R^7$ are previously defined; reacting the product of this reaction with a base to produce the S enantiomer of a compound of formula IV.

An alternative process of the present invention provides a direct enzymatic hydrolysis to produce the R enantiomer of a compound of the formula:

VII

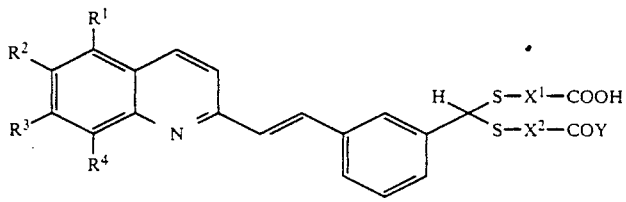

wherein $R^1$, $R^2$, $R^3$ and $R^4$ are independently selected from the group consisting of hydrogen, chlorine, fluorine or bromine; $X^1$ and $X^2$ are independently selected from the group consisting of a $C_1$-$C_8$ straight or branch chained alkyl, a $C_2$-$C_8$ straight or branch chained alkenyl, or a $C_2$-$C_8$ straight or branch chained alkynyl, and Y is $NR^6R^7$ where $R^6$ and $R^7$ are independently selected from the group consisting of hydrogen, a $C_1$-$C_8$ straight or branch chained alkyl, a $C_2$-$C_8$ straight or branch chained alkenyl, a $C_2$-$C_8$ straight or branch chain alkynyl;

which process comprises:
reacting an effective amount of an enzyme with a racemic mixture of a compound of the formula:

VIII

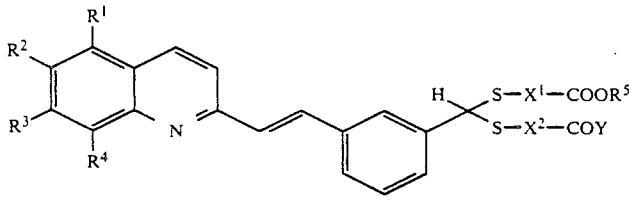

wherein $R^1$, $R^2$, $R^3$, $R^4$, $X^1$, $X^2$ and Y are as previously defined; and $R^5$ is a $C_{1-8}$ straight or branched chained alkyl, a $C_{2-8}$ straight or branch chained alkenyl, a $C^{2-8}$ straight or branch chained alkynyl, $-CH_2COOCH_2CH_3$, $-CH_2CONH_2$; $-CH_2CON(CH_2CH_3)_2$, $CH_2CH_2OCH_3$, $-CH_2CN$ or

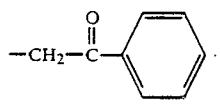

The present invention relates to processes for preparing compounds that have activity as leukotriene and SRS-A antagonists or inhibitors. Because of their activity as leukotriene antagonists or inhibitors, the compounds of the present invention are useful as anti asthmatic, anti allergic, and anti inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina. The compounds of the present invention are useful in the treatment of inflammatory and allergic diseases of the eye, including allergic conjunctivitis. The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol induced hemorrahagic erosions; hepatic ischemic; noxious agent induced damage or necrosis of hepatic, pancreatic, renal, or myocardial tissue; liver parenchymal damage caused by hepatoxic agents such as $CCl_4$ and D-galactosamine; ischemic renal failure; disease induced hepatic damage; bile salt induced pancreatic or gastric damage; trauma- or stress-induced cell damage; and glycerol induced renal failure.

DETAILED DESCRIPTION OF THE INVENTION

Generally, one process of the present invention involves reacting a substituted dithioacetal quinoline prochiral diester with an enzyme which results in enzymatic hydrolysis of one of the esters to form the corresponding substituted dithioacetal quinoline chiral monoester. The substituted dithioacetal quinoline chiral monoester is then reacted with either an amine and a trialkyl aluminum compound to form the R enantiomer of the compound, or reacted with an amine, an acid activating agent, and a base, to form the S enantiomer of the compound. In addition, the present invention also provides a process for preparing the R enantiomer of a substituted dithioacetal quinoline by a direct enzymatic hydrolysis of a racemic mixture of a substituted dithioacetal quinoline monoester.

Enzymes are used in one process of the present invention to form a substituted dithioacetal quinoline chiral monoester intermediate. The enzymes which can be used include but are not limited to esterases, peptidases or lipases. An example of an esterase which can be used in the process of the present invention is pig liver esterase. An example of a peptidase which can be used in this process is chymotrypsin.

The most preferred group of enzymes which can be used in the process of the present invention are lipases. This group includes but is not limited to Pseudomonas species lipase, *Candida cylindracea* lipase and Chromobacterium lipase. These enzymes can be in the crude or purified form and are commercially available. The preferred enzyme to be used is Pseudomonas species lipase in either the crude or purified form.

The enzymatic hydrolysis process of the present invention to form the substituted dithioacetal quinoline chiral monoester intermediate can be conducted at temperatures of from about 10° C. to 80° C., preferably 20° C. to 40° C., and should be accompanied by sufficient stirring of the reaction medium to ensure that thorough mixing of the solid and liquid phases is obtained and then maintained throughout the reaction process.

The reaction time for this enzymatic hydrolysis process is from about 1 hour to 60 hours, however the reaction may proceed for as long as 14 days depending on the temperature and enzyme employed.

The pH of the reaction mixture should be maintained from about 4.5 to about 8 with the optimum pH being 7. A buffer can be employed to maintain the pH of the reaction mixture in the desired range. The buffer used can be a phosphate buffer or any other buffer known in the art.

After the enzymatic hydrolysis of the substituted dithioacetal quinoline prochiral diester to form the corresponding substituted dithioacetal quinoline chiral monoester, the monoester can be reacted to form either the R or S enantiomer of the compound of formula IV.

To form the R enantiomer, the substituted dithioacetal quinoline chiral monoester is reacted with a substituted amine of formula $HNR^6R^7$ where $R^6$ and $R^7$ are previously defined and a trialkyl aluminum compound of the formula $AlR^8R^9R^{10}$ where $R^8$, $R^9$ and $R^{10}$ are previously defined.

To form the S enantiomer, the substituted dithioacetal quinoline chiral monoester is reacted with an acid activating agent and a substituted amine of the formula $HNR^6R^7$ where $R^6$ and $R^7$ are previously defined. The acid activating agent can be, for example, carbonyl diimidazole, 2 chloro-1-methyl pyridinium iodide or ethyl chloroformate. The preferred acid activating agent is carbonyl diimidazole. This leads to the formation of a substituted dithioacetal quinoline chiral monoester of the formula

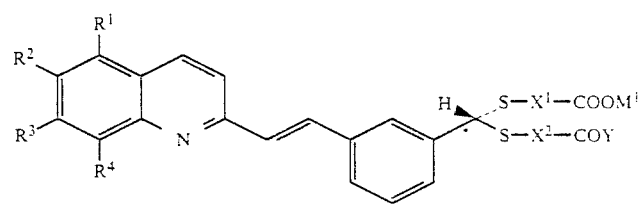

IX wherein $R^1$, $R^2$, $R^3$, $R^4$, $X^1$, $X^2$, Y and $M^1$ are as previously defined.

The compound of formula IX is then reacted with a base such as lithium hydroxide, sodium hydroxide, sodium carbonate or sodium methoxide. The preferred base is lithium hydroxide. This results in the formation of the S enantiomer of the compound of formula IV.

The reaction scheme can be represented as follows:

SCHEME I

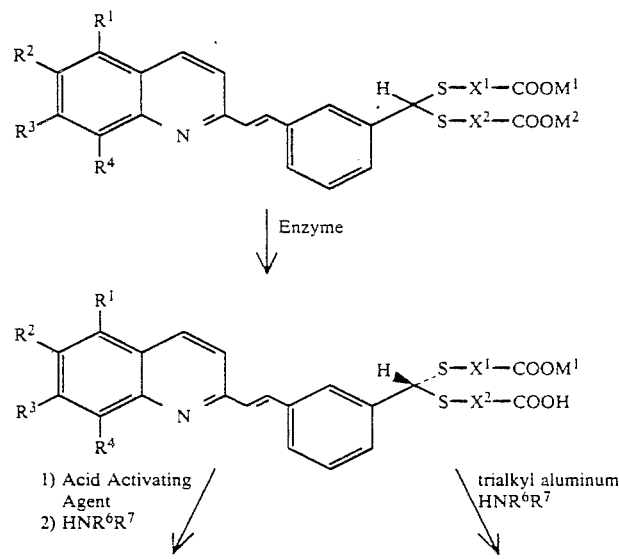

-continued
SCHEME I

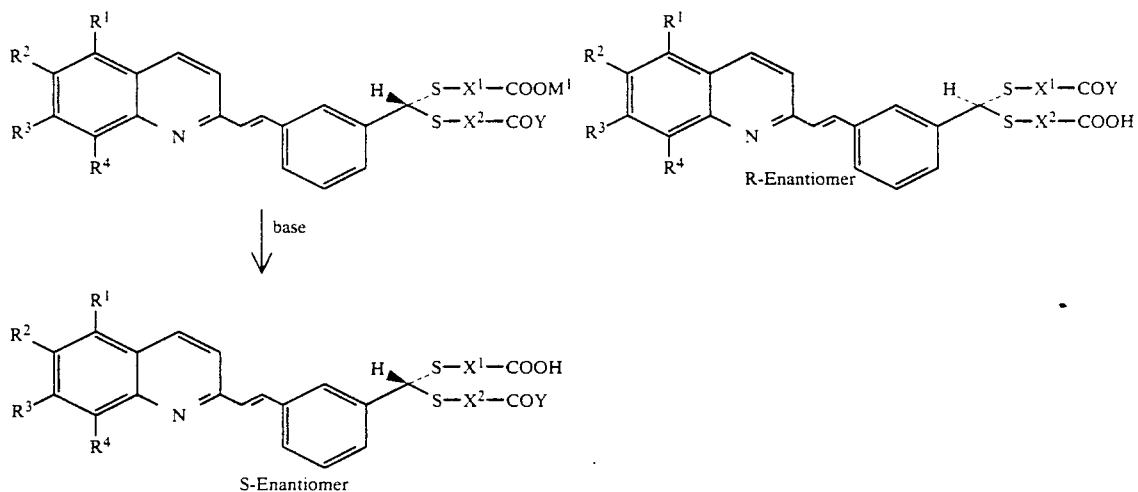

S-Enantiomer

In an alternative process of the present invention the R enantiomer of a substituted dithioacetal quinoline is formed by a direct enzymatic hydrolysis of a substituted dithioacetal quinoline monoester. The enzymes used in this process include but are not limited to esterases peptidases or lipases. An example of an esterase which can be used in this process is pig liver esterase. An example of a peptidase which can be used in the process is chymotrypsin. The most preferred group of enzymes which can be used in this process are lipases This group includes but is not limited to Pseudomonas species lipase, *Candida cylindracea* lipase and Chromobacterium lipase. These enzymes can be in the crude or purified form and are commercially available. The preferred enzyme for this one step enzymatic hydrolysis is *Candida cylindracea* lipase in either the crude or purified form.

The one step enzymatic hydrolysis process can be conducted at temperatures of from about 10° to 80° C., preferably 20° to 40° C., and should be accompanied by sufficient stirring of the reaction medium to ensure that thorough mixing of the solid and liquid phases is obtained and then maintained throughout the reaction process.

The reaction time for this one step enzymatic hydrolysis process is from about 1 hour to 60 hours, however the reaction may proceed for as long as 14 days depending on the temperature and enzymes employed. The pH of the reaction mixture should be maintained from about 4.5 to about 8 with the optimum pH being 7. A buffer can be employed to maintain the pH of the reaction mixture in the desired range. The buffer used can be a phosphate buffer or any other buffer known in the art.

In this alternative one step enzymatic hydrolysis process a racemic 50/50 mixture of the R and S enantiomers of a substituted dithioacetal quinoline monoester is reacted with an enzyme to produce a mixture which is 50% unreacted starting material (S enantiomer) and 50% of the R enantiomer of a substituted dithioacetal quinoline substituted amide carboxylic acid.

The reaction scheme can be represented as follows:

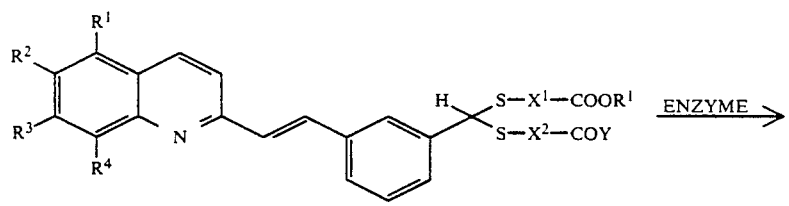

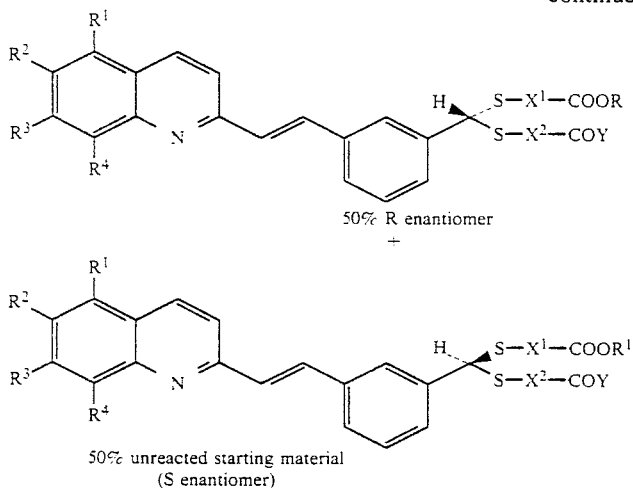

50% R enantiomer
+
50% unreacted starting material
(S enantiomer)

One embodiment of the present invention involves the following steps:
(1) 5-(3-(2-(7-chloroquinolin-2-yl)ethenyl)phenyl)-4,6-dithianonanedioate methyl diester is reacted with Pseudomonas lipase resulting in the enzymatic hydrolysis of one of the methyl esters to form 5-(3-2-(7-chloroquinolin-2-yl)ethenyl)phenyl)-4,6-dithianonemedioate methyl ester carboxylic acid;
(2) The product of step 1 is reacted with trimethylaluminum and dimethylamine to form (R)-5-(3-(2-(7-chloroquinolin-2-yl)ethenyl)phenyl-4,6-dithianonanedioate N,N-carboxylic acid; or the product of step 1 is reacted with carbonyl diimidazole and dimethylamine to form 5-(3-(2-(7-chloroquinolin 2-yl)ethenyl)phenyl-4,6-dithianonanedioate methyl ester N,N-dimethylamide, which is then reacted with lithium hydroxide to form (S)-5-(3-(2-(7-chloroquinolin-2-yl)ethenyl)phenyl)-4,6-dithianonanedioate N,N-dimethylamide carboxylic acid.

In another embodiment of the present invention 5-(3-(2-(7-chloroquinolin-2-yl)- ethenyl)-phenyl)-4,6 dithianonanedioate N,N dimethylamide diethylaminocarboyl methyl ester (i.e., compound VII, where $R^5$ is $-CH_2CON(CH_2CH_3)_2$) is reacted with Candida cylindracea lipase and a phosphate buffer to produce (R)-5-(3-(2-(7-chloroquinolin 2-yl)ethenyl)-phenyl)-4,6 dithianonanedioate N,N diethylamide carboxylic acid as the major product of the reaction.

The following examples should be considered as not limiting the invention and will serve to illustrate the manner in which the present invention is accomplished. All temperatures are in °C.

EXAMPLE 1

S-5-(3-(2-(7-chloroquinolin-2-yl)ethenyl)phenyl)-4,6-dithianonanedioate methyl ester carboxylic acid To a one liter, 3-neck round bottom flask equipped with a pH probe and a mechanical stirrer were added 5-(3-(2-(7-chloroquinolin-2-yl)-ethenyl) phenyl)-4,6-dithianonanedioate methyl diester (30.3 g, 0.059 mol), crude lipase from Pseudomonas species (Amano lipase P-30)(90.5 g), Triton X-100 (9.3 g), Na$_2$HPO$_4$ (10.0 g), and distilled water (592 g). The pH was adjusted to 7.3 using HCl. The reaction mixture was warmed to 40° C. and stirred vigorously for 23 hours. During this period the pH was maintained in the range 6.8 to 7.3 by periodic addition of 5N NaOH. At the end of the age, the pH was adjusted to 4.5 by addition of HCl. Then 300 mL of tetrahydrofuran was added and the mixture was warmed to 60° C., and hot filtered through a bed of Solka Floc. The 2 layers of the filtrate were separated and the organic layer was concentrated to an oil. The oil was crystallized by stirring 16 hours at ambient temperature and 3 hours at 5° C. in 500 mL i-ProH/50 mL water to provide 21.2 g of S-5-(3-(2-(7-chloroquinolin-2-yl)ethenyl)-phenyl)- 4,6-dithianonanedioate methyl ester carboxylic acid of 95% chemical purity (68% yield). HPLC assay indicated 16% of S-5-(3-(2-(7-chloroquinolin-2-yl) ethenyl)-phenyl)-4,6-dithianonanedioate methyl ester carboxylic acid remained in the mother liquors (combined yield 84%) S-5-(3-(2-(7-chloroquinolin 2-yl)-ethenyl)-phenyl)-4,6-dithianonanedioate methyl ester carboxylic acid was derivatized with R-(+)-1-(1-naphthyl)ethylamine using ethyl chloroformate and triethylamine in THF solution. HPLC analysis (C8 column, 80/20 CH$_3$CN/water, 1.5 mL/min, λ=350 nm, retention times 25, 26 min) showed an optical purity of 95%. Recrystallization from i-PrOH increased the optical purity to 98%; $[\alpha]_D^{25} = -5.0(C=2,THF)$

EXAMPLE 2

S-5-(3-(2-(7-chloroquinolin-2-yl)ethenyl)phenyl)-4,6-dithianonanediate N,N-dimethylamide carboxylic acid To a 250 mL round bottom flask were added 5-(3-(2-(7-chloroquinolin-2-yl)ethenyl)-phenyl)-4,6-dithianonanedioate methyl ester carboxylic acid (10.0 g, 95% pure, 0.019 mol) and tetrahydrofuran (100 mL). After cooling to 3° C., 1,1'-carbonyldiimidazole (10,25 g, 0.063 mol) was added and the solution was aged 1 hour at 3° C. Then, a stream of Me$_2$NH was bubbled into the solution for 5 minutes at 3° C.

After further aging 10 minutes, 100 mL ethyl acetate was added the solution was washed with sat. NaHCO$_3$ and brine, dried over MgSO$_4$, and evaporated to an oil. Tetrahydrofuran (80 mL) was added and the solution was cooled to 3° C. A solution of LiOH·H$_2$O (0.80 g, 0.019 mol) in water (20 mL) was added over a 15 minutes period, keeping the reaction mixture at 4°-5° C. After 2.5 hours, solid LiOH·H$_2$O (0.15 g, 0.012 mol) was added. After another 2.5 hours, solid LiOH·H$_2$O (0.25 g, 0.006 mol) was added and the reaction aged at 3° C. another 4.5 hours. At the end of the age, 150 mL water was added and the pH was adjusted to 3.9 using HCl. Ethylacetate (100 mL) and tetrahydrofuran (80 mL) were added and the mixture was stirred 1 minute. The organic layer was separated, washed with brine, dried over MgSO$_4$ at 3° C., and evaporated to an oil. The oil was dissolved in THF (30 mL) and chromatographed on 450 g silica gel (mesh 230-400) using 1% acetic acid in ethyl acetate. The rich cut was concentrated to an oil, flushed twice with toluene (20 mL) to remove acetic acid, and crystallized from i-PrOH (300 mL) for 36 hours at ambient temperature. After vacuum drying for 8 hours at 55° C., 6.9 g (71% yield) was isolated, $[\alpha]_D^{25} = -4.9°$ (C=2, THF). The optical purity was 98% based on the previously described HPLC assay using compound derivatized with S-(−)-1-(1-naphthyl)ethylamine. The chemical purity based on gradient HPLC was 99%.

EXAMPLE 3

R-5-(3-(2-(7-chloroquinolin-2-yl)ethenyl)phenyl)-4,6-dithianonanedioate N,N dimethylamide carboxylic acid To a 100 mL round bottom flask under N$_2$ was added anhydrous dimethylamine hydrochloride (4.11 g, 0.050 mol.) and 25 ml anhydrous toluene. The solution was cooled to −30° C. and a 2M solution of trimethylaluminum in toluene (25 mL, 0.050 mol) was added over a 15 minute period. The solution was slowly warmed to room temperature over a 1 hour period and aged 1 hour at ambient temperature.

To a 250 mL round bottom flask was added 5-(3-(2-(7-chloroquinolin-2-yl)ethenyl)phenyl)-4,6-dithiano-nanedioate methyl ester carboxylic acid (10.0 g, 95% purity, 0.019 mol) and dichloromethane (100 mL). The solution was cooled to 3° C. The solution of trimethyl-aluminum dimethylamine complex (prepared as described in the previous paragraph) was added to the half ester solution over a 10 minutes period at 3° C. The mixture was then warmed to room temperature for 5 hours, then 40° C. for another 15 hours. The reaction was quenched by slowly adding it to an ice cold solution containing 10% aq. KH$_2$PO$_4$ (300 mL), THF (200 mL), and EtOAc (200 mL). This was stirred 0.5 hours at 3° C., then for 1 hour at 40° C. The organic layer was separated, washed with brine, dried with MgSO$_4$, filtered through Solka-Floc, and rotary evaporated. The resulting oil was chromatographed and crystallized as described above for the R-isomer to give 5.7 g of 96% chemical purity (55% yield). The material was purified to 98% purity by recrystallization from methyl ketone (120 mL). The ee was 99%.

EXAMPLE 4

S-5-(3-(2-(7-chloroquinolin-2-yl)ethenyl)phenyl)-4,6-dithianonanedioate methyl ester carboxylic acid 5-(3-(2-(7-chloroquinolin-2-yl)ethenyl) phenyl)-4,6-dithianonanedioate methyl diester (5.27 g), Triton X-100 (5.0 g), Na$_2$HPO$_4$ (7.10 g), Pseudomonas sp. lipase (Sigma purified (0.020 g), and 500 mL water were added to a 1-liter round bottom flask. The pH was adjusted to 7.3 using phosphoric acid, and the mixture was stirred at 37° C. for 14 days. Then, the pH was adjusted to 4.5 and the reaction stirred an additional 5 hours. The mixture was then filtered to provide, after drying under vacuum at 55° C., 4.85 g of S-5-(3-(2-(7-chloroquinolin-2-yl)ethenyl)phenyl)-4, 6-dithianonanedioate methyl ester carboxylic acid with 97% chemical purity (92% yield). HPLC analysis of derivatized material showed an ee of 99%. The specific rotation $[\alpha]_D^{25}$ was −5.0 (C=2, THF).

EXAMPLE 5

S-5-(3-(2-(7-chloroquinolin-2-yl)ethenylphenyl-4,6-dithianonanedioate amino carbonyl methyl ester carboxylic acid 5-(3-(2-(7-chloroquinolin-2-yl)ethenyl)phenyl)-4,6-dithianonanedioate diaminocarbonyl methyl ester (0.20 g), Triton X-405 (3.1 g), crude Candida cylindracea lipase (Sigma) (0.25 g) and 30 mL of 0.1 M phosphate buffer (pH 7.5) were stirred at 21° C. for 20 hours. The pH was lowered to 4.5 and the solution extracted with THF/EtOAc (25 mL each). The organic layer was washed with brine, dried over MgSO$_4$, and concentrated to an oil. The oil was chromatographed on 20 g silica gel using 1% acetic acid in ethyl acetate. The rich cut was concentrated and crystallized from 10 mL i-PrOH to give 55 mg of S-5-(3-(2-(7-chloroquinolin-2-yl)ethenyl)phenyl)-4,6-dithianonane dioate amino carbonyl methyl ester carboxylic acid HPLC of sample derivatized with R-(+)-1-(1-naphthyl)ethylamine showed a 96/4 ratio of enantiomers.

EXAMPLE 6

S-5-(3-(2-(7-chloroquinolin-2-yl)ethenyl)phenyl)-4,6-dithianonanedioate methyl ester carboxylic acid 5-(3-(2-(7-chloroquinolin-2-yl)ethenyl) phenyl)-4,6-dithianonanedioate dimethyl ester (0.20 g), Triton X-405 (2.0 g), purified Chromobacterium viscosum lipase (Sigma) (0.016 g,) and 40 mL of 0.1 M phosphate buffer (pH 7.5) were stirred for 40 hours at 35° C. The reaction proceeded to 70% completion. HPLC analysis of derivatized product showed 99% ee, with the major product being S-5-(3-(2-(7-chloroquinolin-2-yl)e-thenyl)-phenyl)-4,6-dithianonanedioate methyl ester carboxylic acid.

EXAMPLE 7

R-4,5-(3-(2-(7-chloroquinolin-2-yl)ethenyl)phenyl)-3,5-dithiaheptanedioate methyl ester carboxylic acid 4,4-(3-(2-(7-chloroquinolin-2-yl)ethenyl)phenyl)-3,5-dithiaheptanedioate dimethyl ester (0.155 g), Triton X-100 (0.35 g), Candida cylindracea lipase (Sigma crude) (0.39 g), and 12 mL of 0.1 M phosphate buffer (pH 7.5) were stirred 3 hours ambient temperature. Then, the aqueous solution was extracted with 25 mL EtOAc, dried with MgSO$_4$, and concentrated to an oil. The material was derivatized using Et$_3$N, 2-chloro-1-methyl-pyridinium iodide and (S)-(−)-1-(1-naphthyl) ethylamine. HPLC analysis of the derivative showed a 95/5 ratio. The underivatized compound had a (+) rotation.

EXAMPLE 8

6-(3-(2-(7-chloroquinolin-2-yl)ethenyl)phenyl)-5,7-dithiaundecanedioate methyl ester carboxylic acid 6,6-(3-(2-(7-chloroquinolin-2-yl)ethenyl)-phenyl)-5,7-dithiaundecanedioate dimethyl ester (0.10 g), Triton X-100 (0.09 g), purified Pseudomonas sp. lipase (sigma) (0.002 g) and 5 mL of 0.1 M phosphate buffer (pH 7.5) were stirred at room temperature for 60 hours. The product was extracted with 10 mL EtOAc, dried over MgSO$_4$, and concentrated to an oil. The oil was chromatographed on silica gel using 48:48.4 EtOAc:hexane:acetic acid to provide 0.048 g of a pale yellow oil.

The material was derivatized using R-(+)-1-(1-naphthyl)ethylamine and ethyl chloroformate 1Et₃N. HPLC of the derivatized sample showed an 87:13 ratio of isomers.

EXAMPLE 9

6-(3-(2-(7-chloroquinolin-2-yl)ethenyl)phenyl)-5,7-dithiaundecanedioate aminocarbonyl methyl ester carboxylic acid 6-(3-(2-(7-chloroquinolin-2-yl)ethenyl)phenyl)-5,7-dithiaundecanedioate aminocarbonyl methyl ester (0.10 g), Triton X-100 (0.09 g), purified Pseudomonas sp. lipase (sigma) (0.002 g) and 5 mL of 0.1 M phosphate buffer (pH 7.5) were stirred at room temperature for 60 hours. The product was extracted with 10 mL EtOAc, dried over MgSO₄, and concentrated to an oil. The oil was chromatographed on silica gel using 48:48:4 EtOAc:hexane:acetic acid to provide 0.048 g of a pale yellow oil. The material was derivatized using R-(+)-1-(1-naphthyl)ethylamine and ethyl chloroformate and Et₃N. HPLC of the derivatized sample showed an 95:5 ratio of enantiomers.

EXAMPLE 10

R-5-(3-(2-(7-chloroquinolin-2-yl)ethenyl)phenyl)-4,6-

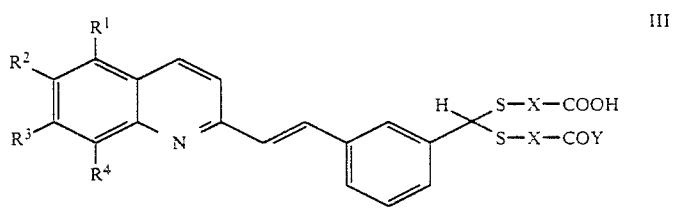

dithianonanedioate N,N-dimethylamide carboxylic acid 5-(3-(2-(7-chloroquinolin-2-yl)ethenyl)-phenyl)-4,6-dithianonanedioate N,N-dimethylamide N,N-diethylaminocarbonyl methyl ester (i.e, compound VIII, where R⁵ is —CH₂CON(CH₂CH₃)₂) (0.083 g), Triton X-405 (0.15 g), *Candida cylindracea* lipase (0.10 g), and 12 mL of 0.1 M phosphate buffer (pH 7.5) were stirred at 21° C. for 52 hours. HPLC analysis of derivatized product showed a 70% ee with the R-enantiomer being the major enantiomer.

What is claimed is:

1. A process for preparing a compound of the formula:

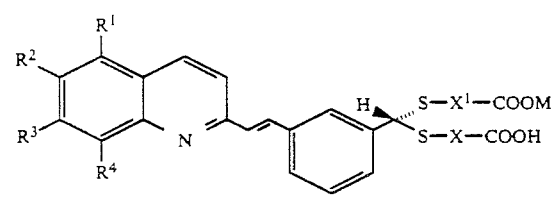

wherein
R¹, R², R³ and R⁴ are independently selected from the group consisting of hydrogen, chlorine, fluorine and bromine;
X is C₁-C₈ straight chained alkyl; and
M is a C₁-C₈ straight or branch chained alkyl, C₂-C₈ straight or branch chained alkenyl, C₂-C₈ straight or branch chained alkynyl, —CH₂COOCH₂CH₃, —CH₂CONH₂, —CH₂CON(CH₂CH₃)₂, or —CH₂CH₂OCH₃; which process comprises reacting an effective amount of an enzyme selected from the group consisting of Pseudomonas lipase, *Candida cylindracea* lipase, and Chromobacterium lipase with a diester compound of the formula:

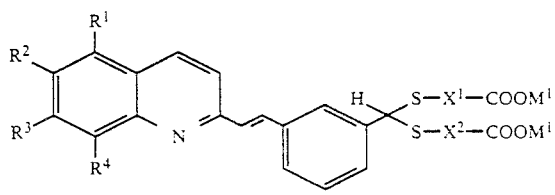

2. The process of claim 1 wherein the enzyme is Pseudomonas lipase and the diester is of the formula II'':

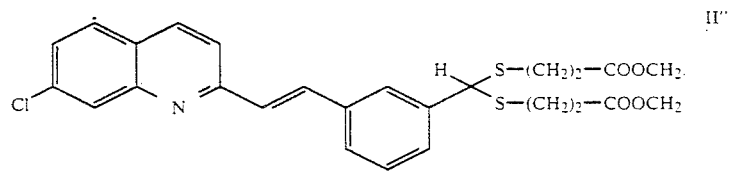

3. A process for preparing the R enantiomer of a compound of the formula:

III

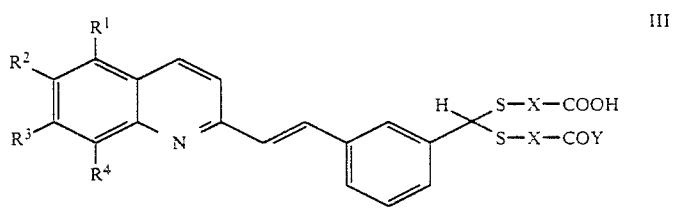

wherein:
R¹, R², R³, and R⁴ are independently selected from the group consisting of hydrogen, chlorine, fluorine and bromine;
R⁶ and R⁷ are independently selected from the group consisting of hydrogen, C₁-C₈ straight or branch chained alkyl, C₂-C₈ straight or branch chained alkenyl, and C₂-C₈ straight or branch chained alkynyl;
X is C₁-C₈ straight chained alkyl; and
Y is —NR⁶R⁷;
which process comprises:
(a) reacting an effective amount of an enzyme selected from the group consisting of Pseudomonas lipase, *Candida cylindracea* lipase, and Chromobacterium lipase with a compound of the formula:

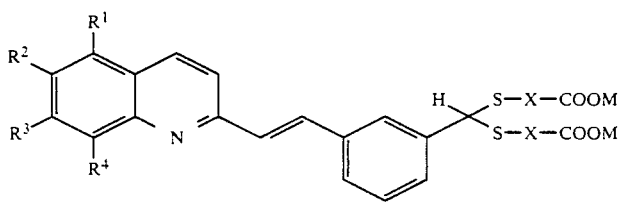

IV wherein:
M is selected from the group consisting of $C_1$-$C_8$ straight or branch chained alkyl, $C_2$-$C_8$ straight or branch chained alkenyl, $C_2$-$C_8$ straight or branch chained alkynyl, $-CH_2COOCH_2CH_3$, $-CH_2CONH_2$, $-CH_2CON(CH_2CH_3)_2$, and $-CH_2CH_2OCH_3$;
to form a compound of the formula:

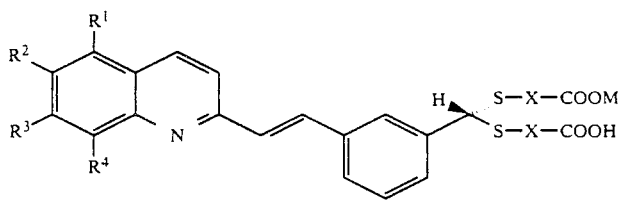

V;

(b) reacting the compound of formula V with an amine of the formula $HNR^6R^7$ and a trialkyl aluminum compound of the formula $AlR^8R^9R^{10}$ where $R^8$, $R^9$, and $R^{10}$ are the same and are a $C_{1-12}$ alkyl group.

4. A process of claim 3 wherein the enzyme is Pseudomonas lipase.

5. A process of claim 4 wherein $R^8$, $R^9$, and $R^{10}$ is each methyl and the compound is of the formula III':

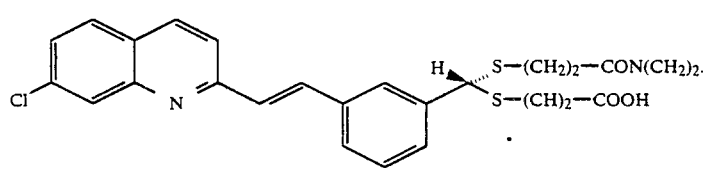

III'

6. A process for preparing the S enantiomer of a compound of the formula:

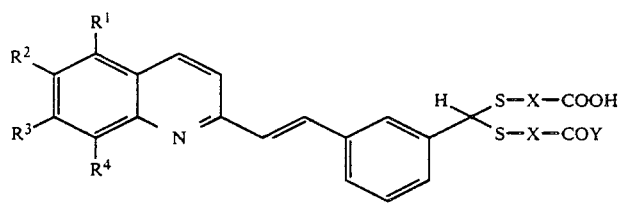

III wherein
$R^1$, $R^2$, $R^3$, and $R^4$ are independently selected from the group consisting of hydrogen, chlorine, fluorine and bromine;
$R^6$ and $R^7$ are independently selected from the group consisting of hydrogen, $C_1$-$C_8$ straight or branch chained alkyl, $C_2$-$C_8$ straight or branch chained alkenyl, and $C_2$-$C_8$ straight or branch chained alkynyl;
X is $C_1$-$C_8$ straight chained alkyl; and
Y is $-NR^6R^7$;
which process comprises:
(a) reacting an effective amount of an enzyme selected from the group consisting of Pseudomonas lipase, *Candida cylindracea* lipase, and Chromobacterium lipase with a compound of the formula:

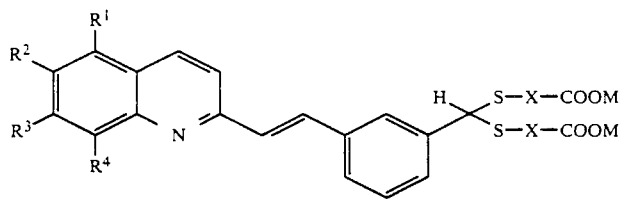

IV wherein:
M is selected from the group consisting of $C_1$-$C_8$ straight or branch chained alkyl, $C_2$-$C_8$ straight or branch chained alkenyl, $C_2$–$C_8$ straight or branch chained alkynyl, —$CH_2COOCH_2CH_3$, —$CH_2CONH_2$, —$CH_2CON(CH_2CH_3)_2$, and —$CH_2CH_2OCH_3$;

to form a compound of the formula:

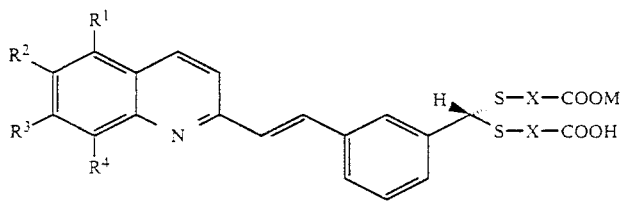

(b) reacting the compound of formula V with an acid activating agent and an amine of the formula $HNR^6R^7$; and then (c) reacting the product of reaction (b) with a base.

7. A process of claim 6 wherein the enzyme is Pseudomonas lipase.

8. A process of claim 7 wherein the compound is of the formula III'':

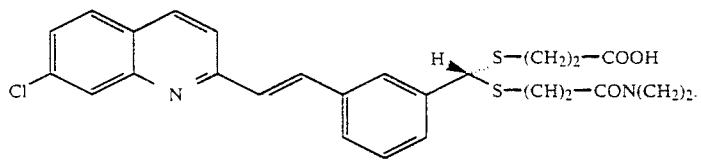

9. A process for preparing the R enantiomer of a compound of the formula:

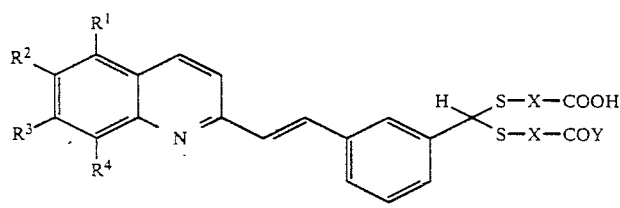

wherein;
$R^1$, $R^2$, $R^3$, and $R^4$ are independently selected from the group consisting of hydrogen, chlorine, fluorine and bromine;
$R^6$ and $R^7$ are independently selected from the group consisting of hydrogen, $C_1$–$C_8$ straight or branch chained alkyl, $C_2$–$C_8$ straight or branch chained alkenyl, and $C_2$–$C_8$ straight or branch chained alkynyl;
X is $C_1$–$C_8$ straight chained alkyl; and
Y is —$NR^6R^7$;
which process comprises reacting an effective amount of an enzyme selected from the group consisting of Pseudomonas lipase, *Candida cylindracea* lipase, and Chromobacterium lipase with a racemic compound of the formula:

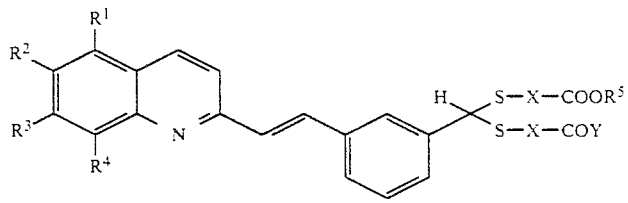

wherein:
$R^1$, $R^2$, $R^3$, and $R^4$ are independently selected from the group consisting of hydrogen, chlorine, fluorine and bromine;
$R^5$ is $C_1$–$C_8$ straight or branched chained alkyl, $C_2$–$C_8$ straight or branch chained alkenyl, $C_2$–$C_8$ straight or branch chained alkynyl, —$CH_2COOCH_2CH_3$, —$CH_2CONH_2$, —$CH_2CON(CH_2CH_3)_2$, $CH_2CH_2OCH_3$, —$CH_2CN$, or

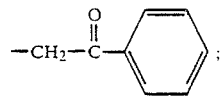

$R^6$ and $R^7$ are independently selected from the group consisting of hydrogen, $C_1$–$C_8$ straight or branch chained alkyl, $C_2$–$C_8$ straight or branch, chained alkenyl, and $C_2$–$C_8$ straight or branch chained alkynyl; and
Y is —$NR^6R^7$.

10. A process of claim 9 wherein the enzyme is *Candida cylindracea* lipase and the racemic compound is of the formula VIII':

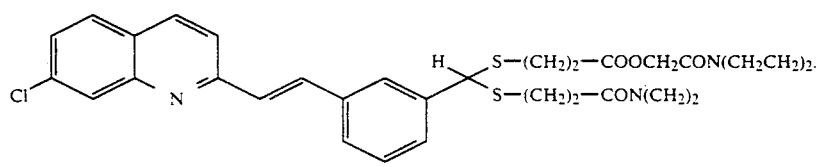
VIII'